US008329954B2

(12) United States Patent  
Sisler

(10) Patent No.: US 8,329,954 B2  
(45) Date of Patent: Dec. 11, 2012

(54) CYCLOPROPENE AMINE COMPOUNDS

(75) Inventor: Edward C. Sisler, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 13/248,917

(22) Filed: Sep. 29, 2011

(65) Prior Publication Data

US 2012/0035269 A1 Feb. 9, 2012

Related U.S. Application Data

(62) Division of application No. 12/138,548, filed on Jun. 13, 2008, now Pat. No. 8,093,430.

(60) Provisional application No. 60/945,777, filed on Jun. 22, 2007, provisional application No. 60/961,183, filed on Jul. 19, 2007.

(51) Int. Cl.
*C07C 211/00* (2006.01)
*C07C 249/00* (2006.01)
*C07C 251/00* (2006.01)
*C07C 257/00* (2006.01)
*C07C 263/00* (2006.01)
*C07C 265/00* (2006.01)
*C07C 267/00* (2006.01)
*A01N 33/00* (2006.01)

(52) U.S. Cl. ........ 564/463; 564/454; 564/305; 564/115; 504/326

(58) Field of Classification Search ........................ None
See application file for complete search history.

(56) References Cited

U.S. PATENT DOCUMENTS

| 5,518,988 A | 5/1996 | Sisler et al. |
| 6,194,350 B1 | 2/2001 | Sisler |
| 6,365,549 B2 | 4/2002 | Sisler |
| 2004/0072694 A1 | 4/2004 | Jacobson et al. |

FOREIGN PATENT DOCUMENTS

WO    WO 01/37663 A2    5/2001

OTHER PUBLICATIONS

Berge et al. "Pharmaceutical Salts", *J. Pharmaceutical Sci.* 66(1):1-19 (1977).
Grichko "New Volatile and Water-Soluble Ethylene Antagonists" *Russian Journal of Plant Physiology* 53(4):523-529 (2006).
Notification of Transmittal of the International Search Report and the Written Opinion of the International Searching Authority, or the Declaration corresponding to International Application No. PCT/US08/007393 mailed Oct. 9, 2008.
Office Action corresponding to Ukrainian Patent Application No. 2010-00591 dated Jul. 13, 2011.
Examination Report corresponding to European Patent Application No. 08768433.8 dated Apr. 8, 2011.

*Primary Examiner* — Johann Richter
*Assistant Examiner* — Clinton Brooks
(74) *Attorney, Agent, or Firm* — Myers Bigel Sibley & Sajovec, PA

(57) ABSTRACT

Methods of applying cyclopropene amine derivatives and compositions thereof to inhibit ethylene receptors in plants and plant material are disclosed. Methods include applying to the plant an effective ethylene response-inhibiting amount of at least one cyclopropene amine compound or composition thereof. Cyclopropene amine compounds, enantiomers, stereoisomers or salts thereof are also provided.

7 Claims, 8 Drawing Sheets

CYCLOPROPENE AMINE COMPOUNDS

RELATED APPLICATION DATA

This application is a divisional application of U.S. application Ser. No. 12/138,548, allowed, filed on Jun. 13, 2008 now U.S. Pat. No. 8,093,430, which claims the benefit of U.S. Provisional Application Ser. No. 60/945,777, filed on Jun. 22, 2007, and U.S. Provisional Application Ser. No. 60/961,183, filed on Jul. 19, 2007. The disclosure of each application is incorporated by reference herein in its entirety.

STATEMENT OF GOVERNMENT SUPPORT

Aspects of this research are supported by the Binational Agricultural Research and Development Fund (BARD) under grant number US-IS-3493-03CR. The U.S. Government has certain rights to this invention.

FIELD OF THE INVENTION

The present invention generally relates to methods of inhibiting ethylene responses in plants and plant materials by applying cyclopropene amine compounds and compositions thereof to plants. The invention further relates to cyclopropene amine compounds, enantiomers, stereoisomers and salts thereof.

BACKGROUND OF THE INVENTION

Ethylene is known to mediate a variety of growth phenomena in plants. See generally Fritz et al. U.S. Pat. No. 3,879,188. This activity is understood to be achieved through a specific ethylene receptor in plants. Many compounds other than ethylene interact with this receptor: some mimic the action of ethylene; while others prevent ethylene from binding and thereby counteract its action.

Many compounds that block the action of ethylene do so by binding to the ethylene binding site. Unfortunately, they often diffuse from the binding site over a period of several hours. See E. Sisler and C. Wood, *Plant Growth Reg.* 7, 181-191 (1988). These blocking compounds may be used to counteract ethylene action. However, a problem with such compounds is that exposure must be continuous if the effect is to last for more than a few hours.

Photoaffinity labeling has been used in biological studies to label binding sites in a permanent manner—usually by generating a carbene or nitrene intermediate. Such intermediates are generally reactive and react rapidly and indiscriminately with many compositions. A compound already bound, however, would react mostly with the binding site. In a preliminary study, it was shown that cyclopentadiene was an effective blocking agent for ethylene binding. See E. Sisler et al., *Plant Growth Reg.* 9, 157-164 (1990). Methods of combating the ethylene response in plants with diazocyclopentadiene and derivatives thereof are described in U.S. Pat. No. 5,100,462 to Sisler et al. U.S. Pat. No. 5,518,988 to Sisler et al. describes the use of cyclopropenes having a $C_1$ to $C_4$ alkyl group to block the action of ethylene.

Notwithstanding these efforts, however, there remains a need in the art for additional methods providing improved plant maturation and degradation regulation as well as those for counteracting ethylene-induced processes in agricultural produce and/or horticultural products.

SUMMARY OF THE INVENTION

The present invention includes cyclopropene compounds of Formula I:

wherein:
n is an integer from 1 to 4;
R is

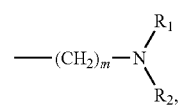

wherein:
m is an integer from 1 to 3,
$R_1$ and $R_2$ are independently hydrogen, $C_1$-$C_5$ alkyl, $C_2$-$C_5$ alkenyl, $C_2$-$C_5$ alkynyl, $C_3$-$C_8$ cycloalkyl, $C_3$-$C_8$ cycloalkenyl, $C_3$-$C_8$ cycloalkynyl, heterocyclyl or aryl, wherein said cycloalkyl, cycloalkenyl, cycloalkynyl, heterocyclyl or aryl is optionally attached to the nitrogen via a $C_1$-$C_5$ alkyl, $C_2$-$C_5$ alkenyl or $C_2$-$C_5$ alkynyl group, or
an enantiomer, stereoisomer or a salt thereof.

In some embodiments, the salt of the compound as described above is selected from the group consisting of phosphate, acetate, formate and carbonate salts.

In particular embodiments, the compound has the following structure:

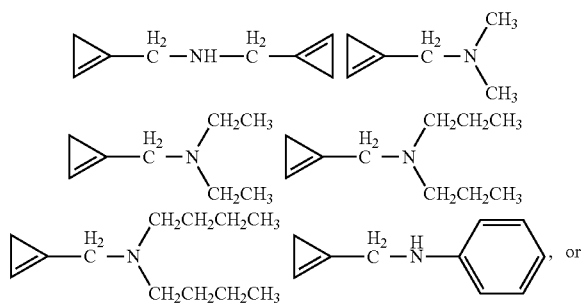

an enantiomer, stereoisomer or a salt thereof.

Embodiments of the present invention further provide compositions including: (a) at least one compound of Formula I; and (b) an adjuvant such as an agriculturally acceptable carrier.

The present invention further includes methods of inhibiting ethylene responses in plants and plant materials. Methods include inhibiting an ethylene response in a plant, comprising applying to the plant an effective ethylene response-inhibiting amount of a compound of Formula I or a composition including at least one compound of Formula I; and an adjuvant.

Application of the compounds to a plant may be carried out by contacting the plant to a gaseous form or salt form of the compound or a mixture thereof, contacting the plant with a solid including the compound, applying a spray including the compound, dipping the plant in a composition including the compound, and addition of the compound to a container containing the plant. Additionally, compounds of the present invention can be applied in an open or closed system. In particular embodiments, compounds of the present invention can be used outside, for example, on field crops or landscaping plants.

Embodiments of the present invention further provide methods of prolonging the life of a cut flower or fresh produce, including applying to the cut flower or fresh produce an effective life-prolonging amount of the cyclopropene amine compounds described herein.

Aspects of the present invention may result in the prolongation of storability and shelf life of produce, such as fruits and vegetables, extension of the storage and vase life of cut flowers, extension of the harvest timing for field crops and/or prolongation of life of landscape plants.

According to further aspects of the present invention, the compounds described herein are useful to provide protection against ethylene regulated processes in vascular plants.

Figure 5:
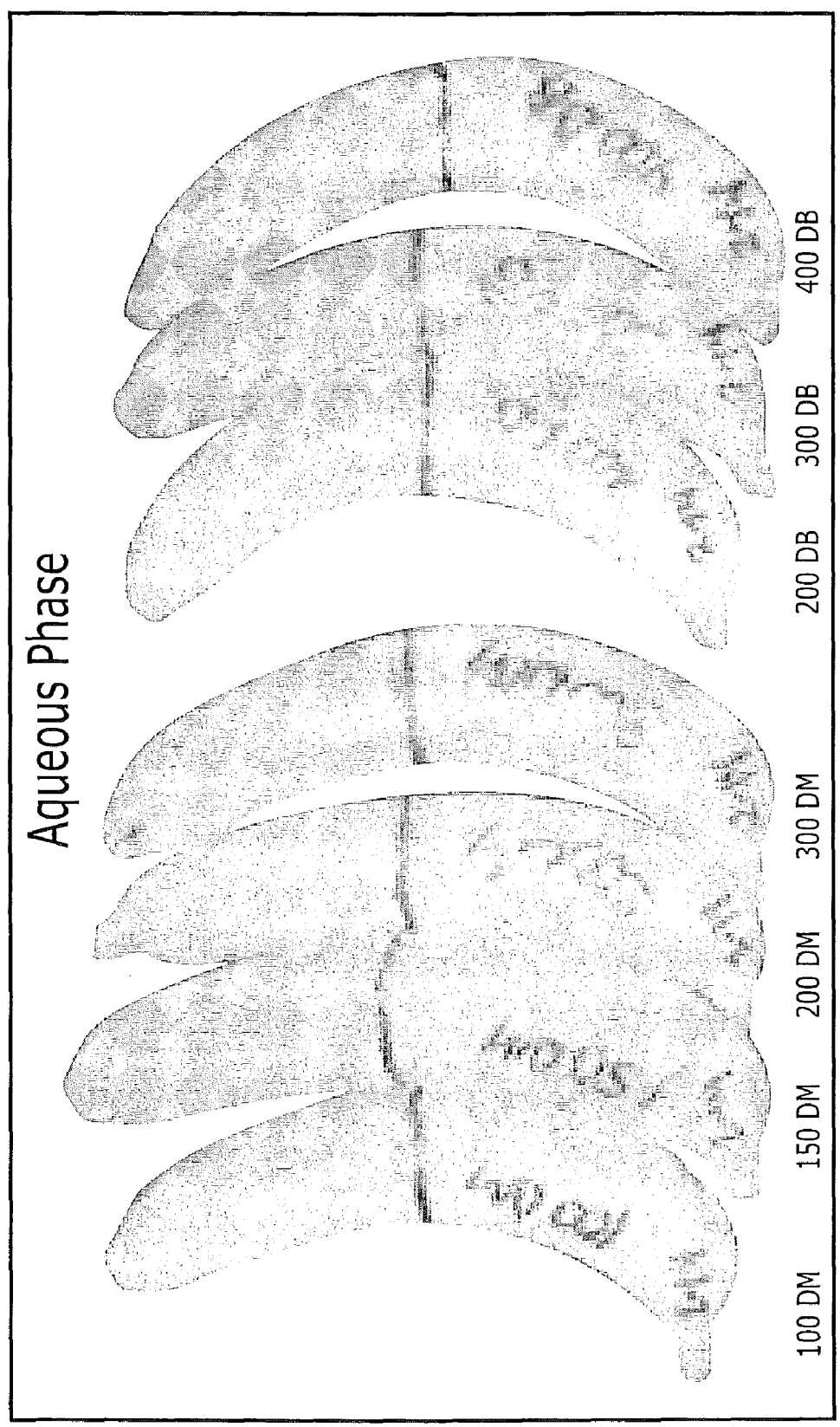
FIG. 5. Aqueous phase. The four bananas on the left show results of the dimethyl compound. The three bananas on the right are results of the dibutyl compound. Compounds were swabbed onto the top half and pictures were taken four days after exposure to ethylene gas. Brown spots on the dibutyl bananas indicate a more extensive ripening, and therefore, less protection after the same number of days. Numbers indicate the µL amount pipetted onto the banana.
Figure 6A:
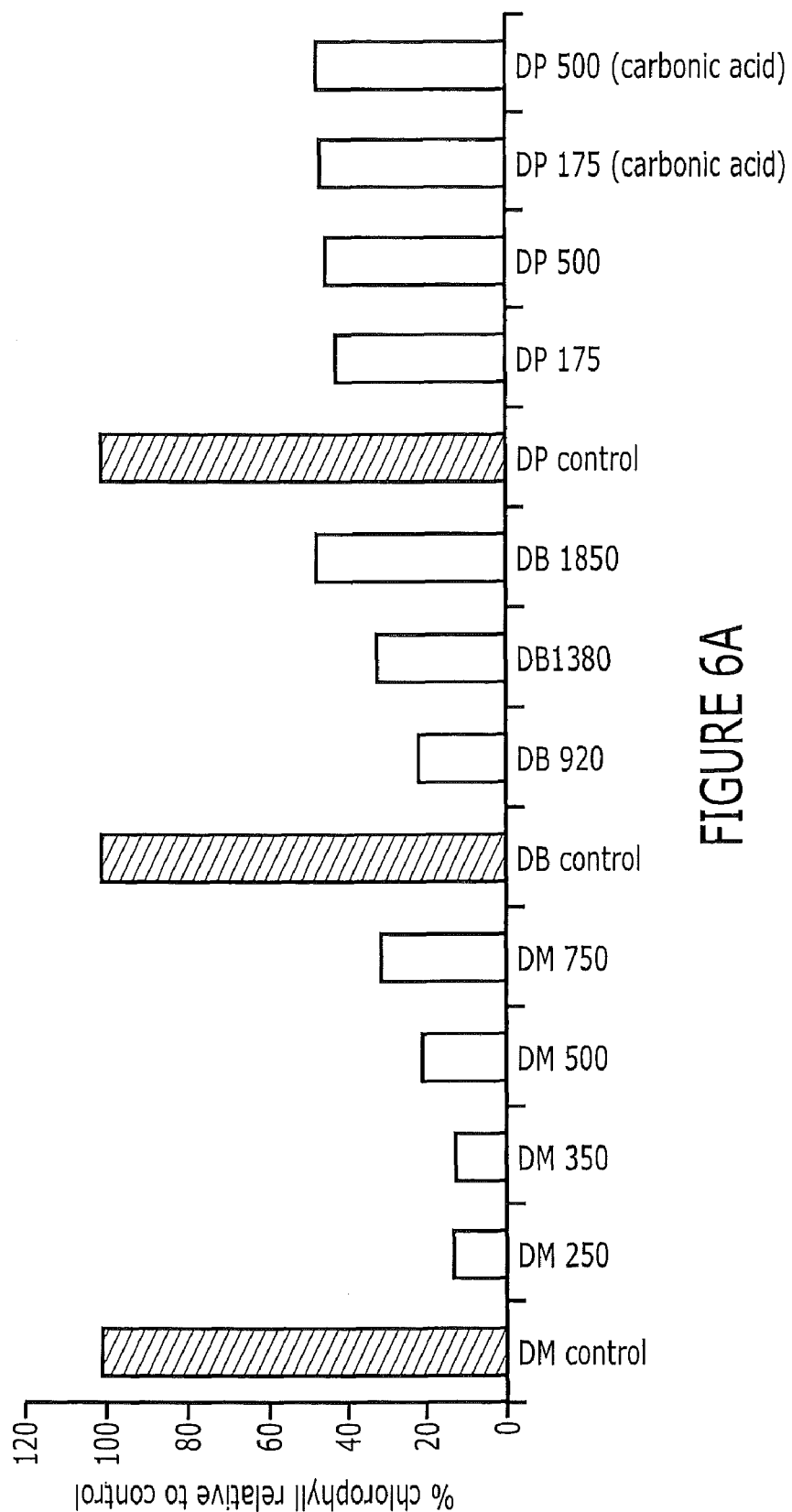
FIG. 6. Results of various compounds. The graph shown in FIG. 6A shows the percent of chlorophyll in banana peels. All but the last two bananas have been treated using acetic acid. A control is considered to be at a 100% chlorophyll level since it has not been treated with compounds or ethylene (ethylene induces ripening). The first black bar is the dimethyl compound control; the following four bars show ascending concentrations to have increasingly higher chlorophyll levels. Higher levels of chlorophyll indicate a higher level of protection because a ripening yellow banana has less chlorophyll than a fresher green banana. The next four show a control for the dibutyl compound along with bananas of ascending concentrations to have increasing levels of chlorophyll. The last set is using the dipropyl compound. The last two bars correspond with the dipropyl compound but were made with carbonic acid.
Figure 6B:
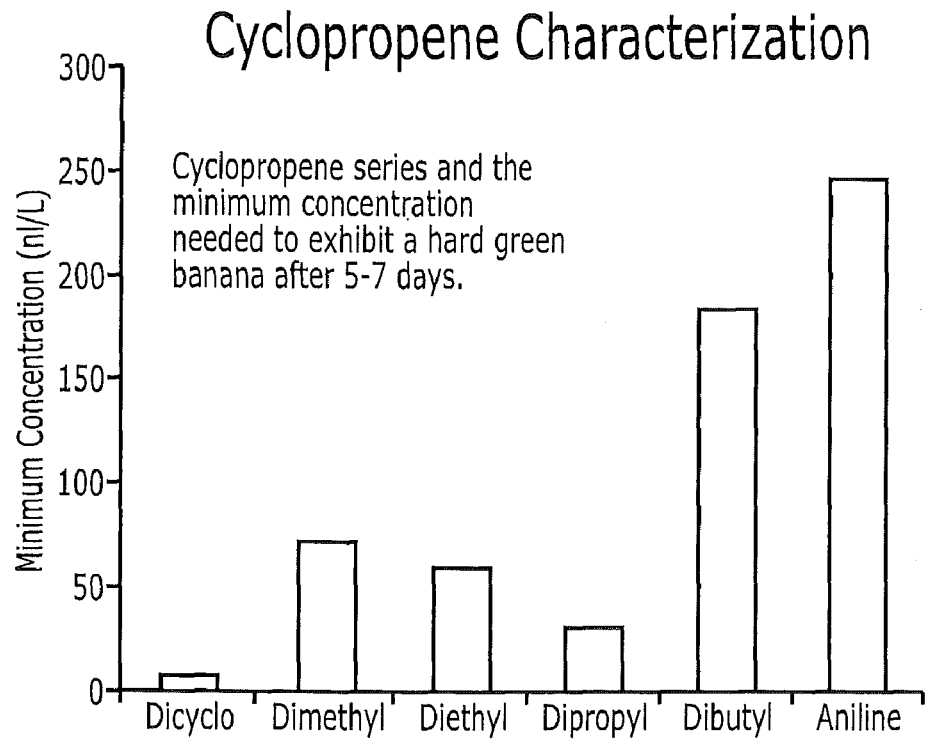
Figure 6C:
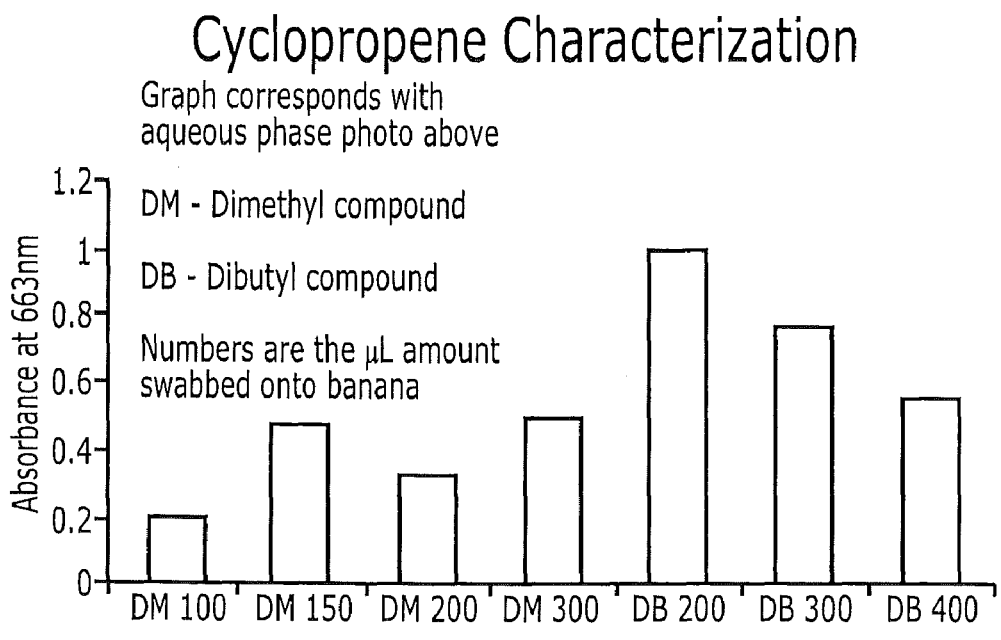

There is a concentration curve among cyclopropene compounds. The last two compounds shown on the graph at FIG. 6B indicate compounds that may be less weak and/or less active. The graph at FIG. 6C shows a numeric version of the aqueous phase picture shown in FIG. 5. The numbers on the y-axis represent the amount of chlorophyll in each banana relative to a control that was left untreated.

Figure 7:

FIG. 7. Protection of flowers (*Krigia dandelion*) by N,N-dipropyl(1-cyclopropenylmethyl)amine (100 nl) as a gas or as the carbonate salt. Treatment included check (control), ethylene, gas form, salt form of N,N-dipropyl(1-cyclopropenylmethyl)amine, from left to right. The flowers were immersed for 48 hours in water or a salt solution. All except check were subjected to ethylene for 24 hours.

Figure 8:
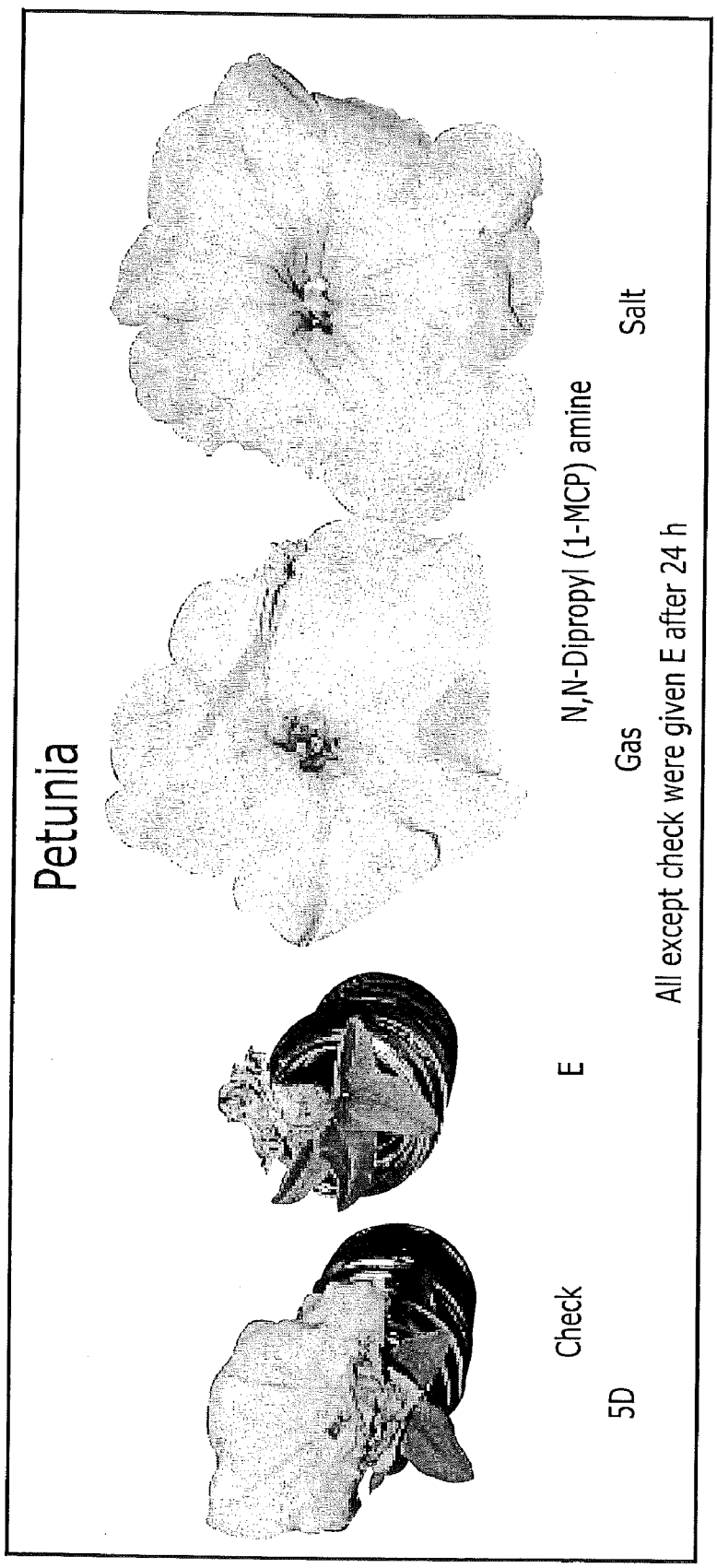

FIG. 8. Protection of flowers (*Petunia hybridia*) by N,N-dipropyl(1-cyclopropenylmethyl)amine (100 nl) as a gas or as the carbonate salt. Treatment included check (control), ethylene, gas form, salt form of N,N-dipropyl(1-cyclopropenylmethyl)amine, from left to right. All except check were subjected to ethylene for 24 hours.

DETAILED DESCRIPTION

The compounds disclosed herein may exhibit significant anti-ethylene activity. In some embodiments, the compound described herein can block the ethylene receptor and may be applied as either a gas or as a salt or as a mixture thereof. Application may be carried out by a spraying or dipping technique. In some embodiments, the compounds can be applied as a salt with a response rate that parallels that of a gaseous form.

Unless otherwise defined, all technical and scientific terms used herein have the same meaning as commonly understood by one of ordinary skill in the art to which this invention belongs. Further, all publications, U.S. patent applications, U.S. patents and other references cited herein are incorporated by reference in their entireties.

The present invention can be practiced based upon the disclosure described herein, in light of the knowledge of persons skilled in the art, and in light of the information set forth in U.S. Pat. No. 6,365,549; U.S. Pat. No. 6,194,350; and U.S. Pat. No. 5,518,988.

Cyclopropene amine compounds that may be used to carry out the present invention may be prepared by using various methods known to those skilled in the art. For example, as described by Baird et al. in *Preparation and Lithiation of 1-Halogenocyclopropenes*, J. CHEM. SOC. PERKIN TRANS. I 1845-53 (1986). Additionally, cyclopropene amine compounds can be prepared using methods described by N. I. Yakushkina and I. G. Bolesov in *Dehydrohalogenation of onohalogenocyclopropanes as a Method for the Synthesis of Sterically Screened Cyclopropenes*, RUSSIAN J. OF ORGANIC CHEM. 15:853-59 (1979).

The cyclopropene amine compounds of the present invention include those of Formula I:

(I)

wherein n is an integer from 1 to 4.

R is

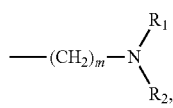

wherein:

m is an integer from 1 to 3. $R_1$ and $R_2$ are independently hydrogen, $C_1$-$C_5$ alkyl, $C_2$-$C_5$ alkenyl, $C_2$-$C_5$ alkynyl, $C_3$-$C_8$ cycloalkyl, $C_3$-$C_8$ cycloalkenyl, $C_3$-$C_8$ cycloalkynyl, heterocyclyl or aryl, wherein said cycloalkyl, cycloalkenyl, cycloalkynyl, heterocyclyl or aryl is optionally attached to the nitrogen via a $C_1$-$C_5$ alkyl, $C_2$-$C_5$ alkenyl or $C_2$-$C_5$ alkynyl group.

In some embodiments, at least one of $R_1$ or $R_2$ is $C_1$-$C_5$ alkyl, $C_2$-$C_5$ alkenyl, $C_2$-$C_5$ alkynyl, $C_3$-$C_8$ cycloalkyl, $C_3$-$C_8$ cycloalkenyl, $C_3$-$C_8$ cycloalkynyl, heterocyclyl or aryl. In further embodiments, m is 1 and in some embodiments, n is 1. In further embodiments, $R_1$ and $R_2$ are independently $C_1$-$C_5$ alkyl. In some embodiments, $R_1$ and $R_2$ are both the same $C_1$-$C_5$ alkyl group. In some embodiments, at least one of $R_1$ or $R_2$ is aryl. In other embodiments, at least one of $R_1$ or $R_2$ is $C_3$-$C_8$ cycloalkenyl and said cycloalkenyl is attached to the nitrogen via a $C_1$-$C_5$ alkyl group.

Embodiments of the present invention further include enantiomers, stereoisomers and salts of the cyclopropene amine compounds described herein.

In some embodiments, the salt of Formula I is selected from the group consisting of phosphate, acetate, formate, carbonate, hydrobromide, hydrochloride, sulfate, bisulfate, nitrate, acetate, trifluoroacetate, oxalate, valerate, oleate, palmitate, stearate, laurate, borate, benzoate, lactate, tosylate, citrate, maleate, fumarate, succinate, tartrate, naphthylate, mesylate, glucoheptonate, lactiobionate and laurylsulfonate salts. In some embodiments, the salt of the Formula I is selected from the group consisting of phosphate, acetate, formate and carbonate salts. In particular embodiments, the salt of Formula I is a carbonate salt.

According to embodiments of the present invention, the compounds are N,N-dicyclopropenylmethylamine, N,N-dimethyl(1-cyclopropenylmethyl)amine, N,N-diethyl(1-cyclopropenylmethyl)amine, N,N-dipropyl(1-cyclopropenylmethyl)amine, N,N-dibutyl(1-cyclopropenylmethyl)amine or N-(1-methylcyclopropene)-aniline. In particular embodiments, the compounds have the following structure:

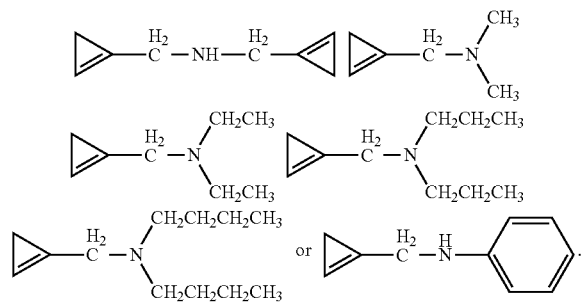

The terms "alkyl", "alkenyl", and "alkynyl", as used herein, refer to linear or branched alkyl, alkenyl or alkynyl substituents, which may be unsubstituted or substituted. Moreover, a range, such as $C_1$-$C_5$, means that the carbon chain can be $C_1$, $C_2$, $C_3$, $C_4$ or $C_5$ or any range inclusive of any of the values included in the range, for example, $C_2$-$C_4$. As used herein, the term "heterocyclyl", "heterocycle" or "heterocyclic" refer to saturated or partially unsaturated monocyclic, bicyclic or tricyclic groups having from 3 to 15 atoms, in some instances 3 to 7, with at least one heteroatom in at least one of the rings. As used herein, "aryl" refers to an aromatic group in a single or fused carbocyclic ring system having from 6 to 15 ring atoms, in some instances 6 to 10, and includes substituted aromatic groups. Examples of aryl groups include, but are not limited to, phenyl, 1-naphthyl, 2-naphthyl and benzyl.

Embodiments of the present invention further include a composition comprising, consisting essentially of or consisting of (a) at least one of a compound of Formula I:

(I)

wherein n is an integer from 1 to 4; R is

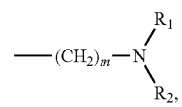

wherein m is an integer from 1 to 3, $R_1$ and $R_2$ are independently hydrogen, $C_1$-$C_5$ alkyl, $C_2$-$C_5$ alkenyl, $C_2$-$C_5$ alkynyl, $C_3$-$C_8$ cycloalkyl, $C_3$-$C_8$ cycloalkenyl, $C_3$-$C_8$ cycloalkynyl, heterocyclyl or aryl, wherein said cycloalkyl, cycloalkenyl, cycloalkynyl, heterocyclyl or aryl is optionally attached to the nitrogen via a $C_1$-$C_5$ alkyl, $C_2$-$C_5$ alkenyl or $C_2$-$C_5$ alkynyl group, or an enantiomer, stereoisomer or a salt thereof; and (b) an adjuvant such as an agriculturally acceptable carrier.

Agricultural compositions including the cyclopropene amine compounds described herein are also encompassed by the invention. In some embodiments, the compositions include 0.005% to 99%, by weight; in other embodiments 1% to 95%, by weight; in further embodiments 2% to 90%, by weight; in still further embodiments 3% to 80%, by weight; and in some embodiments, 4% to 70%, by weight, of the active compounds of the present invention. As used herein, all percentages are percent by weight and all parts are parts by weight, unless otherwise specified, and are inclusive and combinable. All ratios are by weight and all ratio ranges are inclusive and combinable. All molar ranges are inclusive and combinable.

These compositions may include one or more adjuvants, such as, for example, carriers, extenders, binders, lubricants, surfactants and/or dispersants, wetting agents, spreading agents, dispersing agents, stickers, adhesives, defoamers, thickeners, and emulsifying agents. Such adjuvants commonly used in the art can be found in the John W. McCutcheon, Inc. publication Detergents and Emulsifiers, Annual, Allured Publishing Company, Ridgewood, N.J., U.S.A. The term "agriculturally acceptable carrier" refers to adjuvants that are ordinarily used in agricultural formulation technology.

Numerous organic solvents may be used as carriers for the active compounds of the present invention, e.g., hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can also be employed as inert carriers for the active compounds.

The active compounds of the present invention may also include adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour and lignin.

It may be desirable to incorporate a wetting agent in the compositions of the present invention. Such wetting agents may be employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium stearate and potassium oleate, sodium salt of the sulfonated monoglyceride of coconut fatty acids, sorbitan, sesquioleate, lauryl trimethyl ammonium chloride, octadecyl trimethyl ammonium chloride, polyethylene glycol lauryl ether, polyethylene esters of fatty acids and rosin acids (e.g., Ethofat® 7 and 13, commercially available from Akzo Nobel Chemicals, Inc. of Chicago, Ill.), sodium N-methyl-N-oleyltaurate, Turkey Red oil, sodium dibutylnaphthalene sulfonate, sodium lignin sulfonate (Marasperse® N, commercially available from Ligno-Tech USA of Rothschild, Wis.), polyethylene glycol stearate, sodium dodecylbenzene sulfonate, tertiary dodecyl polyethylene glycol thioether, long chain ethylene oxide-propylene oxide condensation products (e.g., Pluronic® 61 (molecular weight 1,000) commercially available from BASF of Mount Olive, N.J.), sorbitan sesquioleate, polyethylene glycol ester of tall oil acids, sodium octyl phenoxyethoxyethyl sulfate, polyoxyethylene (20) sorbitan monolaurate (Tween® 20, commercially available from ICI Americas Inc. of Wilmington, Del.) tris (polyoxyethylene) sorbitan monostearate (Tween® 60, commercially available from ICI Americas Inc. of Wilmington, Del.), and sodium dihexyl sulfosuccinate.

Solid, liquid, and gaseous formulations can be prepared by various conventional procedures. Thus, the active ingredient, in finely divided form if a solid, may be tumbled together with finely divided solid carrier. Alternatively, the active ingredient in liquid form, including mixtures, solutions, dispersions, emulsions and suspensions thereof, may be admixed with a solid carrier in finely divided form. Furthermore, the active ingredient in solid form may be admixed with a liquid carrier to form a mixture, solution, dispersion, emulsion, suspension or the like.

Embodiments of the present invention further include methods of inhibiting an ethylene response in a plant, comprising, consisting essentially of or consisting of applying to the plant an effective ethylene response-inhibiting amount of at least one compound of Formula I:

wherein n is an integer from 1 to 4; R is

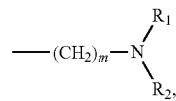

wherein m is an integer from 1 to 3, $R_1$ and $R_2$ are independently hydrogen, $C_1$-$C_5$ alkyl, $C_2$-$C_5$ alkenyl, or $C_2$-$C_5$ alkynyl, $C_3$-$C_8$ cycloalkyl, $C_3$-$C_8$ cycloalkenyl, $C_3$-$C_8$ cycloalkynyl, heterocyclyl or aryl, wherein said cycloalkyl, cycloalkenyl, cycloalkynyl, heterocyclyl or aryl is optionally attached to the nitrogen via a $C_1$-$C_5$ alkyl, $C_2$-$C_5$ alkenyl or $C_2$-$C_5$ alkynyl group, or an enantiomer, stereoisomer, salt or a composition thereof.

In some embodiments, m is 1 and in other embodiments, n is 1. In some embodiments, $R_1$ and $R_2$ are independently $C_1$-$C_5$ alkyl. In further embodiments, $R_1$ and $R_2$ are both the same $C_1$-$C_5$ alkyl group. In some embodiments, at least one of $R_1$ or $R_2$ is aryl. In some embodiments, at least one of $R_1$ or $R_2$ is $C_3$-$C_8$ cycloalkenyl and said cycloalkenyl is attached to the nitrogen via a $C_1$-$C_5$ alkyl group.

In some embodiments, the salt of Formula I is selected from the group consisting of phosphate, acetate, formate, carbonate, hydrobromide, hydrochloride, sulfate, bisulfate, nitrate, acetate, trifluoroacetate, oxalate, valerate, oleate, palmitate, stearate, laurate, borate, benzoate, lactate, tosylate, citrate, maleate, fumarate, succinate, tartrate, naphthylate, mesylate, glucoheptonate, lactiobionate and laurylsulfonate salts. In some embodiments, the salt of Formula I is selected from the group consisting of phosphate, acetate, formate and carbonate salts. In particular embodiments, the salt of Formula I is a carbonate salt.

In some embodiments, when the compounds are applied as a salt, in a non-volatile form, the response rate may parallel that of the gas form. Accordingly, the salt application, in at least some instances, can be used more effectively commercially and the contact between the compound and receptor may be increased.

Additionally, ethylene receptors are thought to form higher-order clusters composed of receptor dimer subunits. The receptor dimers can influence the signaling states of neighboring dimers through direct contact. Accordingly, transmitters from many receptors may be altered by a single ligand-binding event. Some compounds of the present invention can be involved in cross-linking in ethylene receptor clusters.

The active compounds of the present invention can be applied to plants by various suitable means. For example, an active compound may be applied alone in gaseous, liquid, or solid form or a mixture of any combination thereof by contacting the compound with the plant to be treated. Additionally, the active compound may be converted to the salt form, and then applied to the plants. Alternatively, compositions containing one or more active compounds of the present invention may be formed. The compositions may be applied in gaseous, liquid or solid form or a mixture of any combination thereof by contacting the composition with the plant to be treated. Such compositions may include an inert carrier. Suitable solid carriers include dusts. Similarly, when in gaseous form, the compound may be dispersed in an inert gaseous carrier to provide a gaseous solution. The active compound may also be suspended in a liquid solution such as an organic solvent or an aqueous solution that may serve as the inert carrier. Solutions containing the active compound may be heterogeneous or homogeneous and may be of various forms including mixtures, dispersions, emulsions, suspensions and the like.

The active compounds and compositions thereof can also be applied as aerosols, e.g., by dispersing them in air using a compressed gas such as, for example, nitrogen, carbon dioxide, dichlorodifluoromethane, trichlorofluoromethane, or other halocarbons.

Accordingly, in some embodiments, methods of the present invention can be carried out by contacting a plant to a gaseous form of at least one cyclopropene amine compound described herein, contacting said plant to a solid including at least one cyclopropene amine compound described herein, applying a spray including at least one cyclopropene amine compound described herein, dipping the plant in a composition including at least one cyclopropene amine compound described herein, and/or addition of at least one cyclopropene amine compound described herein to a container containing said plant. In some embodiments, the plant is a cut flower.

The present invention can be employed to modify a variety of different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the shortening of the life of ornamentals such as potted plants, cut flowers, shrubbery, and dormant seedlings, in some plants (e.g., pea) the inhibition of growth, and in other plants (e.g., rice) the stimulation of growth. Additional ethylene responses or ethylene-type responses that may be inhibited by active compounds of the present invention include, but are not limited to, auxin activity, inhibition of terminal growth, control of apical dominance, increase in branching, increase in tillering, changing bio-chemical compositions of plants (such as increasing leaf area relative to stem area), abortion or inhibition of flowering and seed development, lodging effects, stimulation of seed germination and breaking of dormancy, and hormone or epinasty effects. Thus, in some embodiments, the cyclopropene amine compounds described herein inhibit one or more of ripening or senescence of flowers, fruits, and vegetables; abscission of foliage, flowers, and fruit; the shortening of life of ornamental plants, cut flowers, shrubbery, seeds, or dormant seedlings; inhibition of growth; stimulation of growth; auxin activity; inhibition of terminal growth; control of apical dominance; increase in branching; increase in tillering; changing the morphology of plants; modifying the susceptibility to plant pathogens such as fungi; changing bio-chemical compositions; inducing pest resistance; abortion or inhibition of flowering or seed development; lodging effects; stimulation of seed germination; breaking of dormancy; hormone effects; and epinasty effects. In some embodiments, the plant is a whole plant and or any portions thereof, a field crop, potted plant, cut flower, or harvested fruit or vegetable. In some embodiments, the ethylene response is fruit ripening, vegetable ripening, and/or flower senescence.

In some embodiments, the compounds can be applied in a closed or open system. In some embodiments, the compounds can be used as a gas in a closed system, for example, indoors or applied to a plant in a container or in a greenhouse. In other embodiments, the compounds can be used a salt, which can be used, for example, in a spray, in an open system, such as outdoors, for example, on field crops or landscape plants.

The term "plant" is used in a generic sense herein, and includes woody-stemmed plants such as trees and shrubs and further includes vascular plants. See also L H Bailey Manual of Cultivated Plants. MacMillan Publishing Company; revised edition (June 1949) for a list of other suitable plants.

Plants to be treated by the methods described herein include whole plants and any portions thereof, field crops, landscape plants, potted plants, cut flowers (stems and flowers), and harvested fruits and vegetables. Accordingly, plants include agricultural produce, such as fresh produce and landscape plants such as trees, shrubs, potted plants and ornamental plants including flowers.

Plants treated with the compounds and by the methods of the present invention are treated with a non-phytotoxic amount of the active compound.

Vegetables which may be treated by the method of the present invention to inhibit ripening and/or senescence include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (*Daucus*), bulbs, such as onions (*Allium* sp.), herbs, such as basil (*Ocimum basilicum*), oregano (*Origanum vulgare*), dill (*Anethum graveolens*), as well as soybean (*Glycine max*), lima beans (*Phaseolus limensis*), peas (*Lathyrus* spp.), corn (*Zea mays*), broccoli (*Brassica oleracea italica*), cauliflower (*Brassica oleracea botrytis*), and asparagus (*Asparagus officinalis*).

Fruits which may be treated by the method of the present invention to inhibit an ethylene response, such as ripening, include tomatoes (*Lycopersicon esculentum*), apples (*Malus domestica*), bananas (*Musa sapientum*), pears (*Pyrus communis*), papaya (*Carica papaya*), mangoes (*Mangifera indica*), peaches (*Prunus persica*), apricots (*Prunus armeniaca*), nectarines (*Prunus persica nectarina*), oranges (*Citrus* sp.), lemons (*Citrus limonia*), limes (*Citrus aurantifolia*), grapefruit (*Citrus paradisi*), tangerines (*Citrus nobilis deliciosa*), kiwi (*Actinidia chinenus*), melons such as cantaloupe (*C. cantalupensis*) and musk melon (*C. melo*), pineapple (*Aranas comosus*), persimmon (*Diospyros* sp.), various small fruits including berries such as strawberries (*Fragaria*), blueberries (*Vaccinium* sp.) and raspberries (e.g., *Rubus ursinus*), green beans (*Phaseolus vulgaris*), members of the genus *Cucumis* such as cucumber (*C. sativus*), and avocados (*Persea americana*).

Ornamental plants that may be treated by the method of the present invention to inhibit an ethylene response, such as senescence and/or shortening of flower life and, thus prolong flower life and appearance (e.g., delay wilting), include potted ornamentals, and cut flowers. Potted ornamentals and cut flowers which may be treated with the present invention include azalea (*Rhododendron* spp.), hydrangea (*Macrophylla hydrangea*), hybiscus (*Hibiscus rosasanensis*), snapdragons (*Antirrhinum* sp.), poinsettia (*Euphorbia pulcherima*), cactus (e.g. *Cactaceae schlumbergera truncata*), begonias (*Begonia* sp.), roses (*Rosa* spp.), tulips (*Tulipa* sp.), daffodils (*Narcissus* spp.), dandelions (*Taraxacum offinale*), petunias (*Petunia hybrida*), carnation (*Dianthus caryophyllus*), lily (e.g., *Lilium* sp.), gladiolus (*Gladiolus* sp.), alstroemeria (*Alstoemeria brasiliensis*), anemone (e.g., *Anemone blanda*), columbine (*Aquilegia* sp.), aralia (e.g., *Aralia chinensis*), aster (e.g., *Aster carolinianus*), bougainvillea (*Bougainvillea* sp.), camellia (*Camellia* sp.), bellflower (*Campanula* sp.), cockscomb (*celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae.

Plants which may be treated by the methods of the present invention to inhibit an ethylene response, such as abscission of foliage, flowers and fruit, include cotton (*Gossypium* spp.), apples, pears, cherries (*Prunus avium*), pecans (*Carya illinoensis*), grapes (*Vitis vinifera*), olives (e.g. *Vitis vinifera* and *Olea europaea*), coffee (*Coffea arabica*), snapbeans (*Phaseolus vulgaris*), and weeping fig (*ficus benjamina*), as well as dormant seedlings such as various fruit trees including apple, ornamental plants, shrubbery, and tree seedlings. In addition, shrubbery which may be treated according to the present invention to inhibit an ethylene response, such as abscission of foliage, include privet (*Ligustrum* sp.), photinea (*Photinia* sp.), holly (*Ilex* sp.), ferns of the family Polypodiaceae, schefflera (*Schefflera* sp.), aglaonema (*Aglaonema* sp.), cotoneaster (*Cotoneaster* sp.), barberry (*Berberis* sp.), waxmyrtle (*Myrica* sp.), abelia (*Abelia* sp.), acacia (*Acacia* sp.) and bromeliades of the family Bromeliaceae.

Field crops which may be treated by the methods of the present invention include a plurality of, or at least more than one, tree, bush, shrub, plant, etc. including the vegetables, fruits, ornamental plants and plants discussed herein.

Active compounds of the present invention have proven to be unexpectedly potent inhibitors of ethylene action on plants, fruits and vegetables, even when applied at low concentrations and varying temperatures. Among other things, compounds of the present invention may result in a longer period of insensitivity to ethylene than compounds found in the prior art. This longer period of insensitivity may occur even when compounds of the present invention are applied at a lower concentration than previous compounds, at varying temperatures and/or when applied as a gas or spray. In some situations, a higher concentration can be used or a longer time interval can be used.

The present invention is explained in greater detail in the following non-limiting examples. In these examples, μl means microliters; ml means milliliters; nl means nanoliters; l means liters; cm means centimeters; and temperatures are given in degrees Celsius.

EXAMPLES

Materials and Methods

1. Preparation of Compounds

A. The preparation of cyclopropene, N,N-dimethyl-(1-cyclopropenylmethyl) amine

The cyclopropene, N,N-dimethyl-(1-cyclopropenylmethyl)amine was prepared from 2-bromo-3-(N,N-dimethyamino)propene. 2-bromo-3-(N,N-dimethyamino)propene was synthesized from 2,3-dibromopropene and dimethylamine by a modified procedure of Corey, et al. (1971) (See E. J. Corey, et. al., The synthesis of racemic α-trans- and β-trans-bergamotene, *J. Am. Chem. Soc.,* 93, 7016-7021 (1971).) 2-bromo-3-(N,N-dimethyamino)propene reacted with bromoform in the presence of 50% NaOH and subsequently reacted with methyllithium to provide the cyclopropene N,N-dimethyl-(1-cyclopropenylmethyl)amine by using the procedure of Al Dulayymi et al. (1996 and 1997) and (Al Dulayymi et al. 1997) (See Al Dulayymi J. R., et al., Structure based interference with insect behaviour-Cyclopropenes analogs of pheromones containing Z-Alkenes, *Tetrahedron,* 52, 12509-12520 (1996); Al Dulayymi A. R., et al., Simple four and five carbon cyclopropane and cyclopropene synthetic intermediates, *Russian. J. Org. Chem.,* 33, 798-816 (1997); Al Dulayymi J. R., et al., Synthesis of Putative ~6-, 12 and ~15-Desaturase Inhibitors, *Tetrahedron,* 53, 1099-1110 (1997)).

B. The preparation of N,N-diethyl-(1-cyclopropenylmethyl)amine, N,N-dipropyl-(1-cyclopropenylmethyl)amine and N,N-dibutyl-(1-cyclopropenylmethyl)amine By applying a similar procedure, N,N-diethyl-(1-cyclopropenylmethyl)amine, N,N-dipropyl-(1-cyclopropenylmethyl)amine and N,N-dibutyl-(1-cyclopropenylmethyl)amine can also be prepared by using the appropriate diamines and 2,3-dibromopropene.

C. The preparation of N,N-dicyclopropenylmethylamine

N,N-dicyclopropenylmethylamine was prepared by a modified procedure of Bottini et al. (1973) and Bottini and Olsen (1973) followed by reaction with bromoform and 50% NaOH and subsequently reacted with methyl lithium by using the procedure of Al Dulayymi et al. (1996) to provide the cyclopropene. (See Bottini A. T. Dey, et al., 2-Bromoallylamine In Organic Synthesis Collective Vol. 5, John Wiley and Sons New York, 121-124, (1973); Bottini, A T, et al., N-(2-bromoallyl)ethylamine In Organic Synthesis Collective Volume 5 John Wiley and Sons New York. 124-126, (1973); Al Dulayymi J. R., et al., Structure based interference with insect behaviour-Cyclopropenes analogs of pheromones containing Z-Alkenes, *Tetrahedron,* 52, 12509-12520 (1996)).

D. The preparation of N-(1-cyclopropenylmethyl)aniline

N-(1-cyclopropenylmethyl)aniline was prepared by a modified procedure of Bottini and Olsen (1973) followed by treatment with 50% NaOH and subsequently with methyl lithium by the procedure of Al Dulayymi et al. (1996) to provide the cyclopropene. (See Bottini, A T, et al., N-(2-bromoallyl)ethylamine In Organic Synthesis Collective Volume 5 John Wiley and Sons New York. 124-126, (1973); Al Dulayymi J. R., et al., Structure based interference with insect behaviour-Cyclopropenes analogs of pheromones containing Z-Alkenes, *Tetrahedron,* 52, 12509-12520 (1996)).

The structures of exemplary cyclopropene amine compounds are further illustrated in Table 1 below.

TABLE 1

| Structure and Name | Minimum Concentration (nl/l) | Protection Time (Days) |
|---|---|---|
| 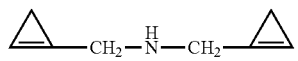 N,N-Dicyclopropenylmethylamine | 5.7 | 33 |
| 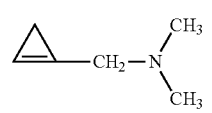 N,N--Dimethyl (1-Cyclopropenylmethyl)amine | 73 | 34 |

TABLE 1-continued

| Structure and Name | Minimum Concentration (nl/l) | Protection Time (Days) |
|---|---|---|
| △—CH₂—N(CH₂CH₃)(CH₂CH₃)<br>N,N--Diethyl (1-Cyclopropenylmethyl)amine | 59 | 32 |
| △—CH₂—N(CH₂CH₂CH₃)(CH₂CH₂CH₃)<br>N,N--Dipropyl (1-Cyclopropenylmethyl)amine | 30 | 33 |
| △—CH₂—N(CH₂CH₂CH₂CH₃)(CH₂CH₂CH₂CH₃)<br>N,N--Dibutyl (1-Cyclopropenylmethyl)amine | 184 | 33 |
| △—CH₂—NH—C₆H₅<br>N-(1-methylcyclopropene)-aniline | 248 | 32 |

Minimum concentration is the amount of compound as a gas in nl/l that would protect bananas by a 24 hour exposure. All bananas remained green for 26-28 days and remained hard for 32-34 days.

2. Plant Material

Untreated mature green bananas (*Musa paradisiaca* L) from Costa Rica which were ready for market were obtained from the local Farmers Market and were kept at 14.5° C. until use. Bananas were used within 24 hours of arrival. Experiments were conducted at approximately 22-23° C. No damaged fruit were used in the experiments.

In experiments to study effects of the compounds described herein on the ethylene response in flowering plants, the petunia (*Petunia hybridia*), a well known ethylene sensitive flower, and the dandelion (*Krigia dandelion*) were used in the experiments.

3. Treatment

To obtain gas phase values, compounds in the gaseous phase were applied to the bananas by pipetting an ether solution of the compound onto filter paper in order to increase the surface area in a 3 liter jar and then allowed to stand for 24 hours to allow the compounds to evaporate and diffuse to the binding site. The jars were then vented and ethylene was injected and allowed to stand for a minimum of 15 hours and then allowed to stand at 23° C. until ethylene responses developed.

When the effect of the respective salts of the cyclopropenes were assayed, the salt was mixed with the desired amount of water containing Tween 20 as a wetting agent and the acid. Usually 200:1 of water, 20:1 of Tween 20 and 100:1 of 0.1 M acid and the compound dissolved in ether were used. These salts were applied to the banana. The peels were swabbed to spread the mixture and increase the exposed surface area. The bananas were placed in an unsealed 3-liter jar and allowed to stand 24 hours. In the case of the carbonate salt, the compound was exposed to carbon dioxide in water long enough for the salt to form. In this case, the carbonate salt was formed by mixing the compound dissolved in water with $CO_2$. The concentration of $CO_2$ in water at 1 atmosphere and 25° C. is reported to be 0.0338 M (Daniels and Alberty 1955) (See Daniels, F, et al., Physical Chemistry, John Wiley and Sons New York, 200 (1955). Only about 1% of the $CO_2$ is present as carbonic acid but equilibrium is fairly rapid and as the carbonic acid is consumed more is produced. Carbonic acid is a much stronger acid than the usually published $pK_a$ of 6.38 would indicate. When corrected for the equilibrium a $pK_a$ value of 3.58 is obtained for carbonic acid (Cotton et al. 1999), which indicates that carbonic acid is generally stronger than formic acid. (See Cotton, et al., Advanced Inorganic Chemistry John Wiley and Sons. New York, 152 (1999). At the end of 24 hours, ethylene was injected and the jars were sealed. After 15 hours exposure, the bananas were removed and observed for several days for the effect of ethylene. An untreated check banana and a similar untreated banana treated with ethylene only were included in each experiment for comparison.

In some studies, only part of the peel was treated. When the peel was exposed to ethylene, the pulp which was not protected began to ripen and produce large amounts of ethylene. The untreated part of the peel ripened quickly but the treated part remained green for many days. In some instances there was a substantial portion of the treated peel green after 18 days.

For gaseous phase treatment, the compound is applied to bananas by pipetting solution onto filter paper. Filter paper is used to increase surface area in a 3 L jar. The jar is sealed for 24 hours to give enough time to diffuse through plant tissue to the ethylene binding sites. 333 ul/L of ethylene gas is added to the jars. The jars are then resealed for 15 hours. This allows for maximal exposure to ethylene to measure effectiveness of the compounds. Firmness was recorded over a number of days. Disappearance of chlorophyll was determined by extracting chlorophyll from banana peels. Absorbance was measured in a spectrometer.

For aqueous phase (salts) treatment, compounds were alternatively tested by mixing the solutions in acid and a detergent. The detergent, Tween 20, was used as a wetting agent. Solutions were then applied at various concentrations to the banana with a cotton swab. Bananas were then sealed in a jar and treated in the same manner as with the gas compound procedures described above.

4. Minimum Amount Required for Protection

The minimum amount of cyclopropene necessary to protect bananas from ethylene was determined after the bananas had been exposed to the compound for 24 hours. Following this time, the fruits were vented for 10 minutes and then exposed to 333 $ul^{-1}$ of ethylene gas treatment. This has been the procedure for most other studies involving cyclopropene compounds and bananas. This time was used so that a reasonable comparison could be made with previous work (Sisler. et al. 1996a; 1996b; 1999; 2001; 2003). (See Sisler E. C., et al., Effect of 1-methylcyclopropene, and methylenecyclopropene on ethylene binding and ethylene action in cut carnations, *Plant Growth Reg.*, 18, 79-86, (1996a); Sisler E. C. et al., Comparison of cyclopropene, 1-MCP and 3,3-dimethylcyclopropene as ethylene antagonist in plants, Plant Growth Reg., 18, 169-174, (1996b); Sisler E. C., et al., Inhibition of ethylene responses by 1-methylcyclopropene and 3-methylcyclopropene, Plant Growth Reg., 27, 105-111 (1999); Sisler, E. C., et al., The effect of chemical structure on the antagonism by cyclopropenes of ethylene responses in banana, Plant Growth Reg., 33, 107-110 (2001); Sisler, E. C., et al., 1-Substituted cyclopropenes: Effective blocking agents for ethylene action in plants, Plant Growth Reg. 40, 221-228 (2003)).

5. Time of Protection

Bananas were treated to an amount of compound believed to saturate the receptor sites (10 times the minimum amount for protection). The bananas were exposed for 24 hours then vented. They were kept on a laboratory bench and each day a sample was exposed to ethylene. The day the bananas were treated with ethylene and the day the bananas turned yellow and became soft were recorded. Generally, this observation occurred about 3 days after the ethylene treatment day. The treatment day the bananas first ripened was considered to be the time of protection.

6. Chlorophyll Determination

Chlorophyll was determined by the method of Arnon (Arnon, D I (1949) Copper content in isolated chloroplasts. Polyphenoloxidase in *Beta vulgaris*. Plant Physiology 24:1-15) or by using a reflective chlorophyll meter (Field Scout CM 1000 Spectronic Technologies Inc.). To extract chlorophyll, a measured area of peel was cut from representative areas of the peel and placed in boiling water for 3 minutes. The samples were then removed and blended with acetone. After standing overnight in the dark, they were filtered then concentrated in a hood and chlorophyll determined by the method of Arnon (1949) according to the procedures outlined by Holden (1965).

7. Gas Chromatography and Spectrophotometry

Gas chromatographic measurements were made on a GP Carbopack C 80/100 0.2% Carbowax 1500 Supelco Supelco Park Bellefonte Park Pa. 16823-0048 Separation was performed according to the procedure of Sisler et al. 2003. (See Sisler, E. C., et al., 1-Substituted cyclopropenes: Effective blocking agents for ethylene action in plants. Plant Growth Reg. 40, 221-228 (2003)).

Banana peel samples were cut and mixed with acetone to extract chlorophyll. Samples were made in an ether solution and absorbance measured at 663 nm.

8. Experimental Results

The effectiveness of the compounds was measured by the amount of chlorophyll present in bananas after some number of days.

A. Effect of Concentration of Cyclopropene Compounds Applied as a Gas

The results of cyclopropenes applied as a gas are reported in Table 1 below. The minimum concentration of the compound N,N-dicyclopropenylmethylamine required for protection of bananas by a 24 hour exposure was 5.3 nl l$^{-1}$ of the compound as a gas. The protection time was 33 days. The minimum concentration of N,N-dimethyl-(1-cyclopropenylmethyl)amine required for protection by a 24 hour exposure was 73 nl.l$^{-1}$ of the compound as a gas. The protection time was 34 days. The minimum concentration of N,N-diethyl (1-cyclopropenyl methyl)amine required for protection by a 24 hour exposure was 59 of the compound as a gas. The protection time was 32 days. The minimum concentration of N,N-dipropyl-(1-cyclopropenylmethyl)amine required for protection by a 24 hour exposure was 30 nl.l$^{-1}$ of the compound as a gas. The protection time was 33 days. The minimum concentration of N,N-dibutyl (1cyclopropenylmethyl) amine required for protection by a 24 hour exposure was 184 nl.l$^{-1}$ of the compound as a gas. The protection time was 33 days. The minimum concentration of N-(1-methylcyclopropene-1-aniline required for protection by a 24 hour exposure was 248 nl.l$^{-1}$ of the compound as a gas. The protection time was 32 days.

B. Effect of Concentration of Cyclopropene on Chlorophyll Content of Banana Peel when Applied as a Salt Experiments were conducted to treat the bananas with the cyclopropene compounds as a salt. Fruit color changes offer some advantages and provide useful information regarding the interaction of the compounds with the ethylene receptor and further provide a good assay system for the compounds to measure diffusion in the tissue.

C. Effect of Different Acids on the Stability of the Cyclopropene Compounds When N,N-dibutyl-(1-cyclopropenylmethyl)amine was incubated with different acids or salts at different pH values down to pH 1.5 for a period of 1 hour, followed by compound re-isolation and use in the usual treatments, little or no inactivation occurred (See Table 2). However, these compounds are thought to be unstable under very acidic conditions. Liao et al. in some synthetic procedures lower the pH to 1-3.

TABLE 2

Effect of pH on stability of N,N-dibutyl-(1-cyclopropenylmethyl)amine.

| Treatment | Chlorophyll (% of control) |
|---|---|
| Gas control | 100 |
| H$_2$O | 98 |
| Sodium acetate (0.1M, pH 4.75) | 100 |
| Sodium formate (0.1M, pH 3.0) | 100 |
| Phosphoric acid (.1M, pH 1.5) | 98 |

Incubated 1 hour at the indicated pH values - and then neutralized with NaOH and extracted with ether. Bananas were exposed to this extract in the usual manner as a gas for 24 hours and then ethylene for 15 hours Readings at 7 days.

D. Effect of Salts on the Application and Protection of the Peel

When a water solution of different salts (phosphate, acetate and formate) of the cyclopropene compound was applied, the peel was protected in all cases. See Table 3 below.

TABLE 3

Effect of pH on N,N-dipropyl-(1-cyclopropenylmethyl)amine salt activity on protection of chlorophyll in bananas.

| Treatment | Chlorophyll (% of control) |
|---|---|
| Control | 100 |
| DP Gas | 100 |

TABLE 3-continued

Effect of pH on N,N-dipropyl-(1-cyclopropenylmethyl)amine salt activity on protection of chlorophyll in bananas.

| Treatment | Chlorophyll (% of control) |
| --- | --- |
| 0.1M Acetic acid | 31 |
| 0.1M Acetic acid buffer (pH 4.75) | 33 |
| 0.1M Formic acid | 30 |
| Phosphoric acid (pH 1.5) | 30 |

The sample was applied with a swab to ½ banana with 20 µl of Tween 20 and water to 200 µl for 24 hours and then exposed to ethylene for 15 hours. Readings made at 5 days.

These did not differ much in effect. At high levels where the acid was in excess, injury occurred with some salt-acid mixtures. Up to 0.2 M acid concentrations did not seem to cause injury.

Figure 1:
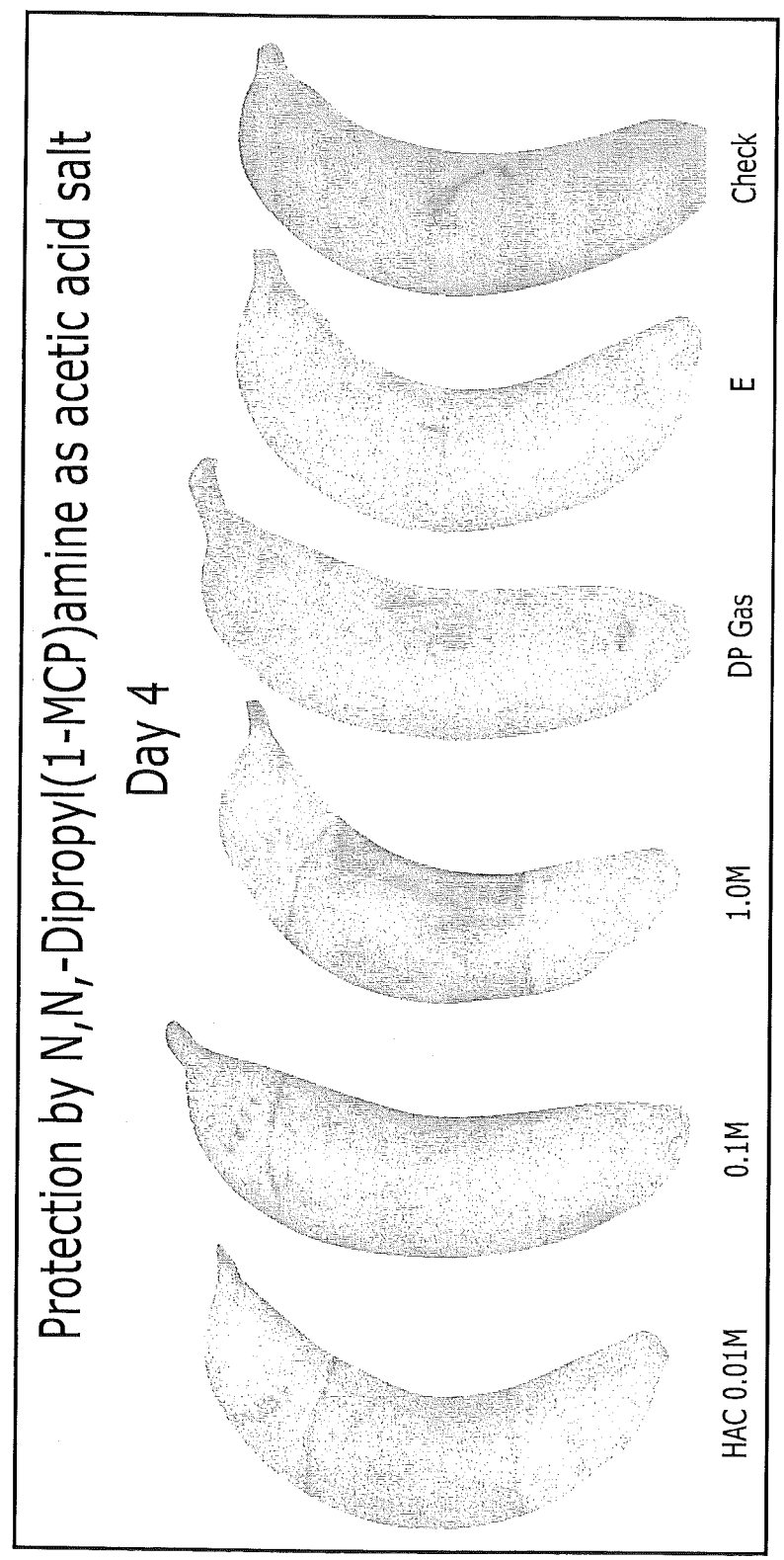
FIG. 1. Protection of banana peel by N,N-dipropyl(1-cyclopropenylmethyl)amine as acetic acid salt.
Figure 2:
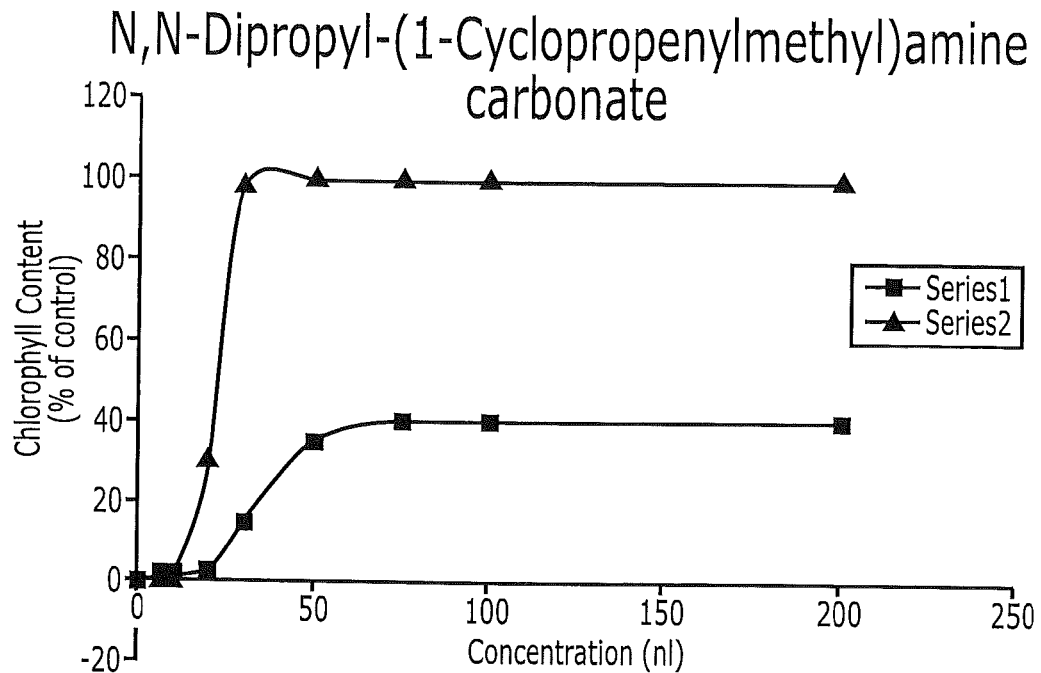
FIG. 2. Protection of banana peel by N,N-dipropyl(1-cyclopropenylmethyl)amine as a gas or as the carbonate salt. The amount of chlorophyll was measured 7 days after the treatment with the compound and 6 days after the treatment with ethylene.

Some experiments were conducted using the carbonate salt (see Table 4 below). It appeared to be as effective as the other acids, and it has the advantage of not leaving a residue if an excess of acid is applied. Any excess is likely to be lost rapidly as carbon dioxide. Other acids can be used. Generally, those with a pH above 1.0 are suitable. When one-half of the banana was treated and the other half was not treated with the compound, the treated half was protected and the untreated half was not. The untreated peel ripened when exposed to ethylene. The peel covering the half of the banana treated with the compound did not ripen when the amount of the compound was sufficiently high for protection. (FIG. 2). If an amount of surface equivalent to one-half of the banana was treated in the middle of the banana, both ends ripened upon exposure to ethylene but the treated portion did not. These results show that the salts penetrate the peel surface and may inactivate the receptor. There did not appear to be diffusion from the applied area into areas that had no cyclopropene compound applied. The pulp of the banana ripened in the treated fruits. Ethylene treatment (300 µl $l^{-1}$) started after 24 hours and lasted 15 hours. This protocol should have stopped the action of the unbound cycloprenes rapidly and essentially stopped any further inactivation of the receptors.

TABLE 4

Comparison of N,N-dipropyl-(1-cyclopropenylmethyl)amine acetate and carbonate salts on chlorophyll content of banana peel.

| Treatment | Chlorophyll (% of Control) |
| --- | --- |
| Untreated control | 100 |
| Carbonic acid + 200 µl dipropyl compound | 48 |
| Carbonic + 50 µl dipropyl compound | 47 |
| Acetic acid + 200 µl dipropyl compound | 46 |
| Acetic acid + 50 µl dipropyl compound | 43 |
| Ethylene | 0 |

Exposure was to the dipropyl compound for 24 hours and after venting 15 hours to ethylene (300 µl/l) Chlorophyll values were taken 5 days after the ethylene was added.

Figure 3:
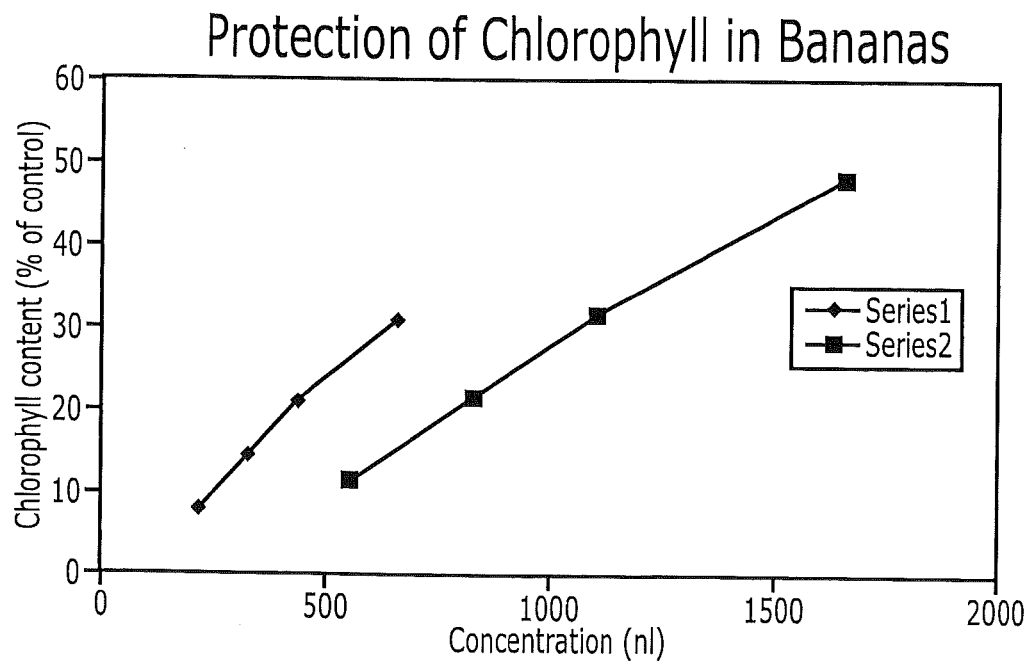
FIG. 3. Effect of N,N Dimethyl(1-cyclopropenylmethyl) amine and N,N Dibutyl(1-cyclopropenylmethyl)amine acetate salts on protecting chlorophyll degradation in banana peel. The treatment levels of 4 samples each were adjusted so that each had equal activities for the compound as a gas. The lowest sample in each case would be equal in activity to a minimum protection level as a gas. Exposure was for 24 hours then ethylene was applied.
Figure 4:
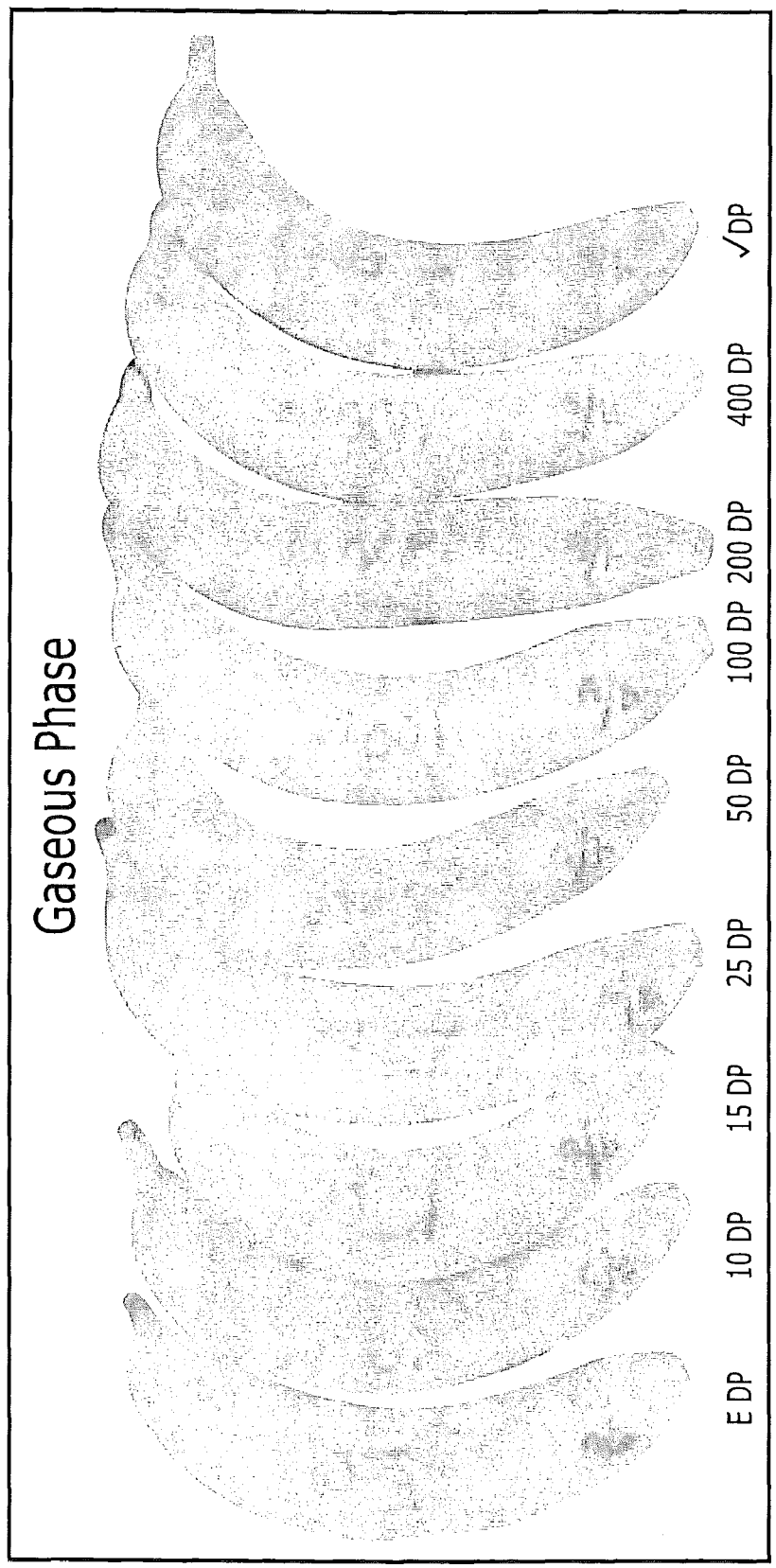
FIG. 4. Gaseous phase. These bananas show results of the gas compound exposure to the dipropyl compound after seven days. Marked with an E, the banana is treated with only ethylene—This shows the fastest ripening since no compound has been applied. Higher concentrations of the compound show more extensive ethylene blockage by comparing the level of green intensity. The check mark represents the control that has remained completely untreated. 10 and 15 µL of the dipropyl compound had already begun showing an ethylene response.

In FIG. 3, the lines represent a comparison between N,N-dimethyl-(1-cyclopropenyl methyl)amine and N,N-dibutyl-(1-cyclopropenylmethyl)amine in their uptake and protection of bananas against ethylene. The compounds were applied on an equal activity basis in a series of concentrations starting at 219 nl for the dimethyl compound and 552 nl for the dibutyl cyclopropene. Each of these were increased by 0, 5× for the second point and also 0.5× for third point and by 1× for the fourth point. The series in both cases would be 1, 1.5, 2, and 2.5. The initial point in both cases was 3 times the minimum for the compound as a gas (see Table 1). Since the activity of the volume of the gas of the jar in determining the minimum value is 3 L, the amount used in the first point would be close to the minimum value for amount of the gas to protect the banana. The lowest of the applied compounds started at 3 times the minimum protection value of 73 nl $l^{-1}$ and 184 nl $l^{-1}$ given in FIG. 3. Each point in the two series should have the same activity as the counterpart point in the other series. The lines resemble each other except in one respect. The difference between the highest and lowest value for the dimethyl cyclopropene was 30.9% of the control and the dibutyl cyclopropene was 48% of the control. The dibutyl compound appears to inactivate the receptor at all concentrations during a 24 hour exposure according to the amount present. It is 1.55× more rapid than the dimethyl compound.

E. Effect of Compounds of Flowering Plants

FIGS. 7 and 8 present the results of using 100 nl N,N-dipropyl(1-cyclopropenylmethyl)amine on dandelions and petunias, respectively. The *Krigia dandelion* is commonly known as a weed that can be found along roads during particular times of the year such as spring and summer. It is of interest because ethylene can cause the plant to become dormant and, as a defense mechanism, the plant can become dormant when there is drought. As shown in FIG. 7, at 5 days, the dandelion treated with the compound, using either a gas or carbonate salt form, shows that these compounds can be used to regulate physiological processes in dandelions. The petunia is a well-known ethylene sensitive flower. As noted in FIG. 8, at 5 days, the petunia treated with the compound, using either a gas or carbonate salt form, appears to withstand the ethylene response.

REFERENCES

Al Dulayymi J. R., Baird M. S., Simpson M. J. and Nyman S. 1996. Structure based interference with insect behaviour-Cyclopropenes analogs of pheromones containing Z-Alkenes. Tetrahedron 52: 12509-12520.

Al Dulayymi A. R., Al Dulayymi J. R., Baird M. S. and Koza G. 1997. Simple four and five carbon cyclopropane and cyclopropene synthetic intermediates. Russian Jour. Org. Chem. 33: 798-816.

Al Dulayymi J. R., Baird M. S., Dale C. M., Grehan C. M. and Short M. F. 1997 Synthesis of Putative ~6-, 12 and ~15-Desaturase Inhibitors. Tetrahedron 53: 1099-1110 Arnon, D I (1949) Copper content in isolated chloroplasts. Polyphenoloxidase in *Beta vulgaris* Plant Physiology 24:1-15.

Bottini A. T. Dey, V. and Klinck, J 1973 2-Bromoallylamine In Organic Synthesis Collective Volume 5 John Wiley and Sons New York. Pp 121-124.

Bottini, A T and Olsen R E 1973 N-(2-bromoallyl)ethylamine In Organic Synthesis Collective Volume 5 John Wiley and Sons New York. Pp 124-126.

Burg S. P. and Burg E. A. 1967. Molecular requirements for the biological activity of ethylene. Plant Physiol. 42: 144-152.

Corey, E. J. Cane, David E. and Libit, Lawrence (1971) The synthesis of racemic α-trans- and β-trans-bergamotene Jour Amer. Chem. Soc. 93:7016-7021.

Cotton, A E and Wilkinson, G. Murillo, C A and Bochmann (1999) Advanced Inorganic Chemistry John Wiley and Sons. New York, P152.

Daniels, F and Alberty, R A. 1955 Physical Chemistry John Wiley and Sons New York P 200.

Dupille E. and Sisler E. G. 1995. Effect of an ethylene receptor antagonist on carnations and other plant material. In: Ait-Oaubahou A. and El-Otmani M. (eds), Postharvest Physiology, Pathology, and Technologies for Horticultural Commodities: Recent Advances. Institut Agronomique et Veterinare Hassan II, Agadir, Morocco, p 294-301.

Lespieau, R and Bourguel M. 1941 2,3-Dibromopropene In Gilman and Blatt (eds). Organic Synthesis Collective. John Wiley and Sons, New York.

Liao, L Zhang F. Yan, N. Golen, J A and Fox, J M (2004) An efficient and general method for resolving cyclopropene carboxylic acids Tetrahedron 60:1803-1816.

Paulini, K. and Reissig, H. (11994) Synthesis of dipeptides containing novel cyclopropenyl- and cyclopropenyl-substituted β and γ-amino acids Leibigs Ann Chem. 1994:549-554.

Pawlowski, N Lee, D J and Sinnhuber, R. O (1972) Synthesis of 1,2-dialkylcyclopropenes, methyl malvate and methyl sterculate. (Jour Org Chem 37:3245-3248.

Sisler E C and Pian A. (1973) The effect of ethylene cyclic olefins on tobacco leaves Tobacco Science 17:68-72.

Sisler, E C and Yang S F (1984) Anti-ethylene effects of cis-2-butene and cyclic olefins. Phytochemistry 23:2765-2768.

Sisler, E. C and Wood, C. 1988. Interaction of ethylene and $CO_2$. Physiol. Plant. 73:440-444.

Sisler E. C. 1991. Ethylene binding components in plants. In: Mattoo A. K. and Suttle J. C. (eds), The Plant Hormone Ethylene. CRC Press, Boca Raton, Fla., pp. 81-99.

Sisler E. C., Dupille E. and Serek M. 1996a. Effect of 1-methylcyclopropene, and methylenecyclopropene on ethylene binding and ethylene action in cut carnations. Plant Growth Reg. 18: 79-86.

Sisler E. C., Serek M. and Dupille E. 1996b. Comparison of cyclopropene, 1-MCP and 3,3-dimethylcyclopropene as ethylene antagonist in plants. Plant Growth Reg. 18: 169-174.

Sisler E. C., Dupille E., Serek M. and Goren R. 1999. Inhibition of ethylene responses by 1-methylcyclopropene and 3-methylcyclopropene. Plant Growth Reg. 27:105-111.

Sisler, E. C. Serek, M Roh, K. A. and Goren, R 2001 The effect of chemical structure on the antagonism by cyclopropenes of ethylene responses in banana. Plant Growth Reg. 33: 107-110.

Sisler, E. C. Alwan, T, Goren, R. Serek. M. and Aplebaum 2003. 1-Substituted cyclopropenes: Effective blocking agents for ethylene action in plants. Plant Growth Reg. 40: 221-228.

Sisler, E. C., Grichko, V. and Serek, M (2006) Interaction of ethylene and other compounds with the ethylene receptor: Agonists and Antagonists In Ethylene Action in plants N. A. Khan ed. Springer-Verlag Berlin p. 1-34.

The foregoing embodiments and examples are illustrative of the present invention and are not to be construed as limiting thereof. The invention is defined by the following claims, with equivalents of the claims to be included therein.

That which is claimed is:

1. A compound having the following structure:

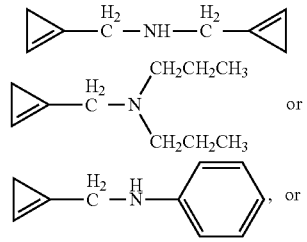

an enantiomer, stereoisomer or a salt thereof.

2. The compound of claim 1, wherein the compound is N,N-dicyclopropenylmethylamine, N,N-dipropyl(1-cyclopropenylmethyl)amine, or N-(1-methylcyclopropene)-aniline.

3. A composition comprising:
(a) at least one of a compound having the following structure:

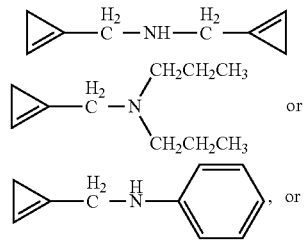

an enantiomer, stereoisomer or a salt thereof; and
(b) an adjuvant.

4. The composition of claim 3, wherein the adjuvant is an agriculturally acceptable carrier.

5. The compound of claim 1, wherein the salt of the compound is selected from the group consisting of phosphate, acetate, formate, carbonate, hydrobromide, hydrochloride, sulfate, bisulfate, nitrate, acetate, trifluoroacetate, oxalate, valerate, oleate, palmitate, stearate, laurate, borate, benzoate, lactate, tosylate, citrate, maleate, fumarate, succinate, tartrate, naphthylate, mesylate, glucoheptonate, lactiobionate and laurylsulfonate salts.

6. The compound of claim 1, wherein the salt of the compound is selected from the group consisting of phosphate, acetate, formate and carbonate salts.

7. The compound of claim 1, wherein the salt of the compound is a carbonate salt.

* * * * *